(12) United States Patent
Kimura et al.

(10) Patent No.: US 7,683,112 B2
(45) Date of Patent: Mar. 23, 2010

(54) PHOSPHITE COMPOSITION AND METHOD FOR PRODUCING THE SAME

(75) Inventors: Kenji Kimura, Toyonaka (JP); Kunihito Miyake, Yamatokoriyama (JP); Hideo Narahara, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 153 days.

(21) Appl. No.: 11/979,910

(22) Filed: Nov. 9, 2007

(65) Prior Publication Data

US 2008/0177005 A1 Jul. 24, 2008

(30) Foreign Application Priority Data

Nov. 10, 2006 (JP) .............................. 2006-305066

(51) Int. Cl.
  *C08K 5/523* (2006.01)
(52) U.S. Cl. .................. 524/117; 524/487; 524/489; 252/400.24
(58) Field of Classification Search ................. 524/117, 524/487, 489; 252/400.24
  See application file for complete search history.

(56) References Cited

U.S. PATENT DOCUMENTS

| 5,985,964 | A | * | 11/1999 | Herbst et al. ................ 524/114 |
| 2007/0108417 | A1 | | 5/2007 | Kimura | |

FOREIGN PATENT DOCUMENTS

| EP | 0 400 454 | 12/1990 |
| EP | 1 788 017 | 5/2007 |
| JP | 2001-81236 | 3/2001 |
| JP | 2006-232905 | 9/2006 |
| WO | 2007/004731 | 1/2007 |

OTHER PUBLICATIONS

European Search Report dated Feb. 6, 2008 in EP Application No. 07 12 0316 corresponding to the present application.

* cited by examiner

*Primary Examiner*—Peter Szekely
(74) *Attorney, Agent, or Firm*—Wenderoth, Lind & Ponack, L.L.P.

(57) ABSTRACT

There is provided a phosphite composition comprising 100 parts by weight of a phosphite represented by the formula (1) and 0.5 to 8 parts by weight of an aliphatic hydrocarbon lubricant having a softening point or a melting point of not higher than 115° C., wherein the content of the phosphite (1) in said composition is 30 to 99.5% by weight.

(1)

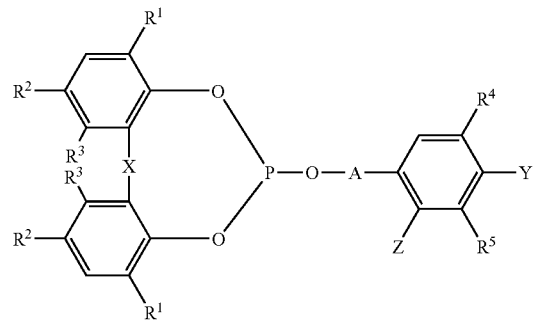

12 Claims, No Drawings

PHOSPHITE COMPOSITION AND METHOD FOR PRODUCING THE SAME

TECHNICAL FIELD

The present invention relates to a phosphite composition.

BACKGROUND OF THE INVENTION

JP-A 10-273494 discloses that a phosphite represented by the formula (1):

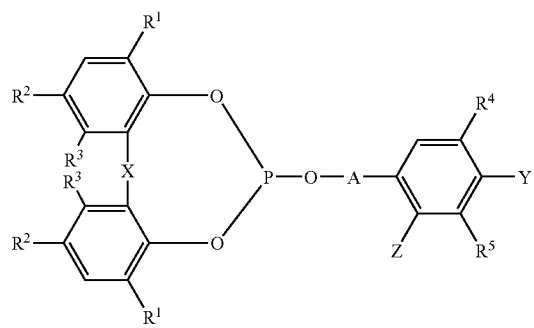

wherein $R^1$, $R^2$, $R^4$ and $R^5$ independently represent a hydrogen atom, an alkyl group of 1 to 8 carbon atoms, a cycloalkyl group of 5 to 8 carbon atoms, an alkylcycloalkyl group of 6 to 12 carbon atoms, an aralkyl group of 7 to 12 carbon atoms or a phenyl group, $R^3$ represents a hydrogen atom or an alkyl group of 1 to 8 carbon atoms, X presents a single bond, a sulfur atom or a —$CHR^6$— group, in which $R^6$ presents a hydrogen atom, an alkyl group of 1 to 8 carbon atoms or a cycloalkyl group of 5 to 8 carbon atoms, A represents an alkylene group of 2 to 8 carbon atoms or a *—$COR^7$— group, in which $R^7$ represents a single bond or an alkylene group of 1 to 8 carbon atoms, and the symbol * represents a point being linked with the oxygen atom of the >P—O— group in the formula (1), one of Y and Z represents a hydroxyl group, an alkoxy group of 1 to 8 carbon atoms or an aralkyloxy group of 7 to 12 carbon atoms, and the other represents a hydrogen atom or an alkyl group of 1 to 8 carbon atoms, when Y is a hydroxyl group, one of $R^4$ and $R^5$ represents an alkyl group of 3 to 8 carbon atoms, a cycloalkyl group of 5 to 8 carbon atoms, an alkylcycloalkyl group of 6 to 12 carbon atoms, an aralkyl group of 7 to 12 carbon atoms or a phenyl group, and $R^1$, $R^2$ and $R^3$ may be the same or different, is for use as an agent for preventing deterioration of a thermoplastic resin such as polyolefin. Specifically, JP-A 10-273494 discloses that a resin composition in a pellet form is obtained by melt-kneading polypropylene together with calcium stearate, which is a metal soap, and a phosphite as additives, and said resin composition slightly undergoes coloring caused by exposure to an NOx gas, that is, has good coloring resistance.

However, the phosphite described in JP-A 10-273494 is usually in a powder form having an average particle diameter of around 20 to 60 μm, so that there is a problem that dust is raised when the phosphite is added to a thermoplastic resin.

For solving such a problem of dust raised upon addition of an additive composition comprising a phosphite and a metal soap, JP-A 2001-81236 discloses that a metal soap and further an organic compound having a lower melting point than that of a metal soap (specifically, glycerin monostearate) as a binder is added to a phosphate metal salt, instead of a phosphite ester, as a main component to obtain a granular additive composition, and said granular additive composition hardly produces dust. In addition, JP-A 2001-81236 discloses that an additive composition containing a lubricant (e.g. polypropylene wax having a molecular weight of 7000 and a melting point of 140° C.) as a binder is hardly dispersed in a thermoplastic resin.

SUMMARY OF THE INVENTION

The present inventors prepared an additive composition as described in JP-A 2001-81236 provided that the main component was a phosphite and glycerin monostearate was added as a binder, and then melt-kneaded a thermoplastic resin together with the additive composition to prepare a thermoplastic resin composition. However, the thermoplastic resin composition had insufficient coloring resistance.

Thus, an object of the present invention is to provide a composition which hardly generates dust and which is easily dispersed in a thermoplastic resin, thereby imparting good coloring resistance to the thermoplastic resin.

Under such circumstances, the present inventors studied intensively and as a result, found that a composition containing a phosphite and a certain lubricant could overcome such problems.

That is, the present invention provides:

[1] a phosphite composition comprising 100 parts by weight of a phosphite represented by the formula (1):

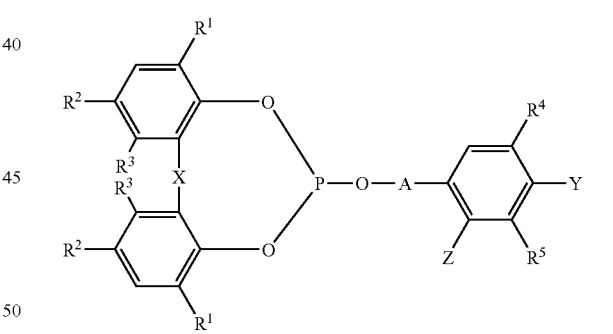

wherein $R^1$, $R^2$, $R^4$ and $R^5$ independently represent a hydrogen atom, an alkyl group of 1 to 8 carbon atoms, a cycloalkyl group of 5 to 8 carbon atoms, an alkylcycloalkyl group of 6 to 12 carbon atoms, an aralkyl group of 7 to 12 carbon atoms or a phenyl group, $R^3$ represents a hydrogen atom or an alkyl group of 1 to 8 carbon atoms, X presents a single bond, a sulfur atom or a —$CHR^6$— group, in which $R^6$ presents a hydrogen atom, an alkyl group of 1 to 8 carbon atoms or a cycloalkyl group of 5 to 8 carbon atoms, A represents an alkylene group of 2 to 8 carbon atoms or a *—$COR^7$— group, in which $R^7$ represents a single bond or an alkylene group of 1 to 8 carbon atoms, and the symbol * represents a point being linked with the oxygen atom of the >P—O— group in the formula (1), one of Y and Z represents a hydroxyl group, an alkoxy group of 1 to 8 carbon atoms or an aralkyloxy group of 7 to 12 carbon atoms, and the other represents a hydrogen atom or an alkyl group of 1 to 8 carbon atoms, when Y is a hydroxyl group, one of $R^4$ and $R^5$ represents an alkyl group of 3 to 8 carbon atoms, a cycloalkyl group of 5 to 8 carbon atoms, an alkylcycloalkyl group of 6 to 12 carbon atoms, an aralkyl group of 7 to 12 carbon atoms or a phenyl group, and $R^1$, $R^2$ and $R^3$ may be the same or different; and 0.5 to 8 parts by weight of an aliphatic hydrocarbon lubricant having a softening point or a melting point of not higher than 115° C., wherein the content of a phosphite represented by the formula (1) in said composition is 30 to 99.5% by weight;

[2] the composition according to the above [1], wherein the aliphatic hydrocarbon lubricant is at least one kind of aliphatic hydrocarbon lubricant selected from the group consisting of liquid paraffin, paraffin having a melting point of 40 to 70° C., and polyethylene wax having a softening point of not higher than 115° C.;

[3] the composition according to the above [1] or [2], which is a granular composition;

[4] the composition according to the above [3], which comprises not more than 10% by weight of components having a particle diameter of not more than 45 μm;

[5] a method for producing a phosphite composition, which comprises mixing 100 parts by weight of a phosphite represented by the formula (1) defined in the above [1] and 0.5 to 8 parts by weight of an aliphatic hydrocarbon lubricant having a softening point or a melting point of not higher than 115° C., and granulating the mixture at a temperature range of 40 to 110° C.;

[6] the method according to the above [5], wherein granulation is carried out at a temperature 3 to 25° C. below the softening point or melting point of the aliphatic hydrocarbon lubricant;

[7] a method of stabilizing a thermoplastic resin, which comprises incorporating 0.01 to 1 part by weight of the composition according to any one of the above [1] to [4] into 100 parts by weight of a thermoplastic resin; and

[8] the method according to the above [7], wherein the thermoplastic resin is polyolefin.

DETAILED DESCRIPTION OF THE PREFERRED EMBODIMENTS

Hereinafter, the present invention will be explained in detail.

A phosphite used in the present invention is a compound represented by the above formula (1) [hereinafter, referred to as the phosphite (1)].

In the formula (1), $R^1$, $R^2$, $R^4$ and $R^5$ independently represent a hydrogen atom, an alkyl group of 1 to 8 carbon atoms, a cycloalkyl group of 5 to 8 carbon atoms, an alkylcycloalkyl group of 6 to 12 carbon atoms, an aralkyl group of 7 to 12 carbon atoms or a phenyl group.

Examples of the alkyl group of 1 to 8 carbon atoms include a methyl group, a t-butyl group, a t-pentyl group, a t-octyl group and the like.

Examples of the cycloalkyl group of 5 to 8 carbon atoms include a cyclopentyl group, a cyclohexyl group, and the like.

Examples of the alkylcycloalkyl group of 6 to 12 carbon atoms include a methylcyclopentyl group, a methylcyclohexyl group, a dimethylcyclohexyl group and the like.

Examples of the aralkyl group of 7 to 12 carbon atoms include a benzyl group and the like.

In the formula (1), $R^3$ represents a hydrogen atom or an alkyl group of 1 to 8 carbon atoms. Examples of the alkyl group of 1 to 8 carbon atoms are the same as those described above.

Preferably, $R^3$ is a hydrogen atom or a methyl group.

In the formula (1), X represents a single bond, a sulfur atom or a —$CHR^6$— group, and $R^6$ represents a hydrogen atom, an alkyl group of 1 to 8 carbon atoms or a cycloalkyl group of 5 to 8 carbon atoms. Examples of the alkyl group of 1 to 8 carbon atoms and the cycloalkyl group of 5 to 8 carbon atoms are the same as those described above.

Examples of the —$CHR^6$— group include a methylene group, an ethylidene group, a propylidene group, a 1-cyclohexylmethyl group and the like. Preferably, X is a single bond, a methylene group or an ethylidene group.

In the formula (1), A represents an alkylene group of 2 to 8 carbon atoms or a *—$COR^7$ group, in which $R^7$ represents a single bond or an alkylene group of 1 to 8 carbon atoms and the symbol * represents a point being linked with the oxygen atom of the >P—O— group in the formula (1). Examples of the alkylene group of 1 to 8 carbon atoms include a methylene group, an ethylene group, a trimethylene group, a tetramethylene group and the like. Preferably, A is an alkylene group of 2 to 4 carbon atoms or the *—$COR^7$— group.

The carbon-carbon bond of the alkylene group of 2 to 4 carbon atoms may be interrupted by a heteroatom-containing group. Examples of the heteroatom-containing group include a —O—C(=O)— group and a —C(=O)—O— group. Preferably, $R^7$ is an alkylene group of 1 to 4 carbon atoms.

In the formula (1), one of Y and Z represents a hydroxyl group, an alkoxy group of 1 to 8 carbon atoms or an aralkyloxy group of 7 to 12 carbon atoms, and the other represents a hydrogen atom or an alkyl group of 1 to 8 carbon atoms. When Y is a hydroxyl group, one of $R^4$ and $R^5$ is preferably an alkyl group of 3 to 8 carbon atoms, a cycloalkyl group of 5 to 8 carbon atoms, an alkylcycloalkyl group of 6 to 12 carbon atoms, an aralkyl group of 7 to 12 carbon atoms or a phenyl group. Examples of the alkoxy group of 1 to 8 carbon atoms include a methoxy group, an ethoxy group, a t-butoxy group and the like. Examples of the aralkyloxy group of 7 to 12 carbon atoms include a benzyloxy group and the like. Examples of the alkyl group of 3 to 8 carbon atoms include an i-propyl group, a t-butyl group, a t-pentyl group, a cycloalkyl group of 5 to 8 carbon atoms, an alkylcycloalkyl group of 6 to 12 carbon atoms and the like. Examples of the aralkyl group of 7 to 12 carbon atoms are the same as those described above.

When Y in the formula (1) is a hydroxyl group, Z is more preferably a hydrogen atom or a methyl group, and one of $R^4$ and $R^5$ is more preferably a t-butyl group.

When Z in the formula (1) is a hydroxyl group, it is preferable that $R^5$ is a methyl group, Y is a hydrogen atom and $R^4$ is a t-butyl group.

In addition, $R^1$, $R^2$ and $R^3$ in the formula (1) may be the same as or different from each other.

Preferable examples of the phosphite (1) include 6-[3-(3-t-butyl-4-hydroxy-5-methylphenyl)propoxy]-2,4,8,10-tetra-t-butyldibenz[d,f][1,3,2]dioxaphosphepine, 6-[3-(3,5-di-t-butyl-4-hydroxyphenyl)propoxy]-2,4,8,10-tetra-t-butyldibenz[d,f][1,3,2]dioxaphosphepine, 6-[3-(3,5-di-t-butyl-4-hydroxyphenyl)propoxy]-4,8-di-t-butyl-2,10-dimethyl-12H-dibenzo[d,g][1,3,2]dioxaphosphocine, 6-[3-(3,5-di-t-butyl-4-hydroxyphenyl)propionyloxy]-4,8-di-t- butyl-2,10-dimethyl-12H-dibenzo[d,g][1,3,2]dioxaphosphocine, and the like.

The phosphite (1) used in the present invention usually comprises not less than 10% by weight of fine particles having a particle diameter of not more than 45 μm, and has an average particle diameter on a weight basis of around 20 to 60 μm.

An aliphatic hydrocarbon lubricant used in the present invention has a softening point or a melting point of not higher than 115° C. The softening point is a value measured according to JIS (Japanese Industrial Standard) K 2531, and the melting point is a value measured according to JIS K 0064-3.1.

When an aliphatic hydrocarbon lubricant having a softening point or a melting point of not higher than 115° C. is used in the present invention, generation of dust from the resulting composition tends to be reduced, and the resulting composition tends to allow a phosphite to be easily dispersed in a thermoplastic resin. Therefore, such an aliphatic hydrocarbon lubricant is desirable in the present invention.

The aliphatic hydrocarbon lubricant is usually a mixture of alkanes having a molecular weight of not more than 6000, and specific examples thereof include liquid paraffin, natural or synthetic paraffin having a melting point of around 40 to 70° C., polyethylene wax having a softening point of not higher than 115° C., partial oxide, fluoride, and chloride of them, and the like.

As the aliphatic hydrocarbon lubricant, a commercially available product may be used as it is. Specific examples of a commercially available aliphatic hydrocarbon lubricant that may be used in the present invention include "Hi-white (manufactured by Nippon Oil Corporation)" of liquid paraffin, "145° Paraffin (melting point 63° C., manufactured by Nippon Oil Corporation)", "140° Paraffin (melting point 62° C., manufactured by Nippon Oil Corporation)", "135° Paraffin (melting point 60° C., manufactured by Nippon Oil Corporation)", "130° Paraffin (melting point 57° C., manufactured by Nippon Oil Corporation)" and "125° Paraffin (melting point 54° C., manufactured by Nippon Oil Corporation)" of paraffin, and the like.

Examples of the polyethylene wax include "Sunwax 131-P (softening point 108° C., manufactured by Sanyo Chemical Industries, Ltd.)", "Sunwax 151-P (softening point 107° C., manufactured by Sanyo Chemical Industries, Ltd.)", "Sunwax 161-P (softening point 111° C., manufactured by Sanyo Chemical Industries, Ltd.)", "Sunwax 165-P (softening point 107° C., manufactured by Sanyo Chemical Industries, Ltd.)", "Sunwax 171-P (softening point 105° C., manufactured by Sanyo Chemical Industries, Ltd.)", "Mitsui Hi-wax 110P (softening point 100° C., manufactured by Mitsui Chemicals, Inc.", "Mitsui Hi-wax 220P (softening point 113° C., manufactured by Mitsui Chemicals, Inc.", and the like.

The aliphatic hydrocarbon lubricant is preferably polyethylene wax because it can suppress consolidation upon storage of a composition.

The composition of the present invention contains 100 parts by weight of the phosphite (1) and 0.5 to 8 parts by weight, preferably 1 to 6 parts by weight of the aliphatic hydrocarbon lubricant. The composition of the present invention may additionally contain not more than 20 parts by weight of a thermoplastic resin.

When not less than 0.5 parts by weight of the aliphatic hydrocarbon lubricant is present in the composition of the present invention, granulation and melting of the composition tend to be easy and pulverization of the composition tends to be suppressed, being preferable. When not more than 8 parts by weight of the aliphatic hydrocarbon lubricant is present in the composition of the present invention, production of granules having a bigger particle diameter tends to be suppressed upon granulation of the composition, and thereby the amount of the phosphite (1) contained in granules tends to be increased, being preferable.

The content of the phosphite (1) in the composition of the present invention is 30 to 99.5% by weight, preferably 50 to 99% by weight.

The composition of the present invention may further contain at least an additive selected from the following additive group: (i) a neutralizing agent, (ii) a lubricant other than a aliphatic hydrocarbon lubricant, (iii) a hindered amine light stabilizer, (iv) an ultraviolet absorbing agent, (v) a metal soap, (vi) an antistatic agent, (vii) an anti-blocking agent, (viii) a pigment, (ix) a flame retardant, (x) a filler, and (xi) an antioxidant including a phenol antioxidant, and a phosphorus antioxidant other than the phosphite (1), as long as the composition of the present invention does not exert adverse influence such as coloration on a thermoplastic resin when the composition is incorporated into the thermoplastic resin.

An additive used in the present invention has an average particle diameter on a weight basis of preferably 0.1 to 100 μm, particularly preferably 0.5 to 70 μm.

When a commercially available additive is used, it is preferable that the additive is adjusted to a preferable average diameter on a weight basis by a known method prior to use.

Examples of the above described additive include the following compounds:

(i) a neutralizing agent such as synthetic hydrotalcite, natural hydrotalcite, calcium hydroxide, aluminum hydroxide, etc.;

(ii) a lubricant such as oleamide, erucylamide, etc.;

(iii) a hindered amine light stabilizer such as bis(2,2,6,6-tetramethyl-4-piperidyl)sebacate, poly[{6-(1,1,3,3-tetramethylbutyl)amino-1,3,5-triazin-2,4-diyl}{(2,2,6,6-tetramethyl-4-piperidyl)imino}-1,6-hexamethylene{(2,2,6,6-tetramethyl-4-piperidyl)imino}], etc.;

(iv) an ultraviolet absorbing agent such as 2-(2-hydroxy-5-methylphenyl)benzotriazole, 2-(3-t-butyl-2-hydroxy-5-methylphenyl)-5-chlorobenzotriazole, 2,4-di-t-butylphenyl 3,5-di-t-butyl-4-hydroxybenzoate, etc.;

(v) a metal soap including a metal salt of fatty acid having a carbon number of 4 to 18, such as a lithium salt, a magnesium salt, a sodium salt, a calcium salt, a barium salt, an aluminum salt, a zinc salt, or an iron salt of stearic acid; a lithium salt, a magnesium salt, a sodium salt, a calcium salt, a barium salt, an aluminum salt, a zinc salt, or an iron salt of palmitic acid; a lithium salt, a magnesium salt, a sodium salt, a calcium salt, a barium salt, an aluminum salt, a zinc salt, or an iron salt of lauric acid; a calcium salt or a zinc salt of behenic acid; a calcium salt, a magnesium salt or a zinc salt of 12-hydroxystearic acid, etc.;

(vi) an antistatic agent including a quaternary ammonium salt-type cationic surfactant, a betaine-type amphoteric surfactant, an alkyl phosphate-type anionic surfactant, a cationic surfactant such as a primary amine salt, a secondary amine salt, a tertiary amine salt, a quaternary amine salt or a pyridine derivative;

an anionic surfactant such as a sulfated oil, a soap, a sulfate ester oil, a sulfated amide oil, a sulfated ester salt of olefin, an aliphatic alcohol sulfuric acid ester salt, an alkylsulfate ester salt, an ethylsulfonate salt of a fatty acid, an alkylnaphthalene sulfonate, an alkylbenzenesulfonate, a sulfonate salt of a succinic acid ester, or a phosphate ester salt;

a nonionic surfactant such as a partial fatty acid ester of a polyhydric alcohol, an ethylene oxide adduct of an aliphatic alcohol, an ethylene oxide adduct of a fatty acid, an ethylene oxide adduct of an aliphatic amino or a fatty acid amide, an ethylene oxide adduct of alkylphenol, an ethylene oxide adduct of a partial fatty acid ester of a polyhydric alcohol, or polyethylene glycol; an amphoteric surfactant such as a carboxylic acid derivative or an imidazoline derivative; and antistatic agents having a melting point exceeding 70° C. among the above described antistatic agents;

(vii) an anti-blocking agent including an inorganic anti-blocking agent such as aluminum silicate, synthetic silica, natural silica, zeolite, kaolin or diatomaceous earth; and an organic anti-blocking agent such as cross-linked polymethylmethacrylate;

(viii) a pigment such as carbon black, titanium oxide, a phthalocyanine pigment, a quinacridone pigment, an isoindolinone pigment, a perylene or perynine pigment, a quinophthalone pigment, a diketopyrrolo-pyrrole pigment, a dioxazine pigment, a fused disazo pigment, a benzimidazolone pigment, etc.;

(ix) a flame retardant such as decabromobiphenyl, antimony trioxide, a phosphorus flame retardant, aluminum hydroxide, etc.;

(x) a filler such as calcium carbonate, silicate, glass fiber, talc, kaolin, mica, barium sulfate, carbon black, carbon fiber, zeolite, metal powder, metal oxide, etc.;

(xi) an antioxidant including a phenol antioxidant such as 2-t-butyl-6-(3-t-butyl-2-hydroxy-5-methylbenzyl)-4-methylphenyl acrylate, 2-[1-(2-hydroxy-3,5-di-t-pentylphenyl)ethyl]-4,6-di-t-pentylphenyl acrylate, 1,3,5-trimethyl-2,4,6-tris(3,5-di-t-butyl-4-hydroxybenzyl)benzene, tris(3,5-di-t-butyl-4-hydroxybenzyl) isocyanurate, 1,3,5-tris(4-t-butyl-3-hydroxy-2,6-dimethylbenzyl)-1,3,5-triazine-2,4,6-(1H,3H,5H)-trione, 2,2'-methylenebis(6-t-butyl-4-methylphenol), 4,4'-butylidenebis (6-t-butyl-3-methyolphenol), 4,4'-thiobis(6-t-butyl-3-methylphenol) etc., and a phosphorus antioxidant other than the phosphite (1), such as tris(2,4-di-t-butylphenyl)phosphite, bis(2,4-di-t-butylphenyl)pentaerythritol diphosphite, bis(2,6-di-t-butyl-4-methylphenyl)pentaerythritol diphosphite, bis(2,4-di-cumylphenyl)pentaerythritol diphosphite, tetrakis(2,4-di-t-butylphenyl)-4,4'-biphenylene diphosphonite, 6-[3-(3-t-butyl-4-hydroxy-5-methylphenyl)propoxy]-2,4,8,10-tetra-t-butylbenz[d,f][1,3,2]dioxaphosphepine, etc.

In the composition of the present invention, the content of the additive excepting a metal soap is usually not more than 100 parts by weight, preferably not more than 70 parts by weight, more preferably not more than 40 parts by weight, relative to 100 parts by weight of the phosphite (1).

The total content of the additives in the composition of the present invention is around 0 to 90% by weight.

It is preferable that the composition of the present invention contains a metal soap. The amount of a metal soap contained in the composition of the present invention is preferably 0.1 to 100 parts by weight, more preferably 0.1 to 40 parts by weight, relative to 100 parts by weight of the phosphite (1).

Examples of the shape of the composition of the present invention include a pellet shape which is made by melt-kneading and then extrusion molding, a granular shape, and the like. A granular composition is easily produced, and has excellent dispersibility in a thermoplastic resin. Thus, when the composition of the present invention in a granular form is added to a thermoplastic resin, the resulting thermoplastic resin composition tends to have improved coloring resistance. Therefore, it is preferable that the composition of the present invention is granular.

Hereinafter, the granular composition of the present invention will be explained.

It is preferable that the granular composition of the present invention contains not more than 10% by weight of components having a particle diameter of not more than 45 μm as measured by a sieve. Thereby, generation of dust from the composition is remarkably suppressed.

For the purpose of reducing the amount of components having a particle diameter of not more than 45 μm, for example, in a process for producing the composition of the present invention, 1 to 8 parts by weight of the aliphatic hydrocarbon lubricant may be used, mixing and granulation of 100 parts by weight of the phosphite and the aliphatic hydrocarbon lubricant may be performed for 20 to 120 minutes, or mixing and granulation of 100 parts by weight of the phosphite and the aliphatic hydrocarbon lubricant may be performed at 50 to 110° C.

The granular composition of the present invention has usually an average particle diameter of 80 to 2000 μm.

When the average particle diameter is not less than 80 μm, generation of dust from the composition tends to be suppressed, being preferable. When the average particle diameter is not more than 2000 μm, dispersibility of the phosphite in a thermoplastic resin tends to become good, being preferable. Particularly preferably, the granular composition of the present invention has an average particle diameter of 90 to 1000 μm.

An average particle diameter, as used in the present invention, is a value obtained by sieving about 5 g of a sample at a vibration of level 8, a shift time of 3 minutes and a pulse interval of 1 second using a robot shifter equipped with a standard sieve complying with JIS Z 8801 (manufactured by Seishin Enterprise Co., Ltd), and then calculating an average particle diameter on a weight basis from the weight of particles remaining in openings of the sieve and on the sieve.

In the present invention, it is not meant that one granule contains the phosphite (1) and the aliphatic hydrocarbon lubricant at the above described weight ratio, but it is meant that the whole granular composition comprises the phosphite (1) and the aliphatic hydrocarbon lubricant at the above described weight ratio.

The term "granular composition" means a population of irregular granules as described in JIS-Z 8841 (1993), Section 10, Table 1 "Shape and Name of Granule".

The granular composition of the present invention is be produced, for example, by adding at least one of the aforementioned aliphatic hydrocarbon lubricants in an amount of 0.5 to 8 parts by weight, preferably 1 to 6 parts by weight, more preferably 2 to 5 parts by weight and optionally an additive to 100 parts by weight of the phosphite (1), and then granulating the mixture at 40 to 110° C.

The temperature for granulation in the present invention is the temperature of a mixture consisting of the phosphite (1), the aliphatic hydrocarbon lubricant, and an additive if present.

A preferable granulation temperature is a temperature about 3 to 25° C. below the softening point or melting point of the aliphatic hydrocarbon lubricant, depending on the softening temperature or melting temperature and the addition amount of the aliphatic hydrocarbon lubricant. When the granulation temperature is a temperature 3° C. or more below the softening point or melting point of the aliphatic hydrocarbon lubricant, pulverization of the resulting composition tends to be suppressed, being preferable. When the granulation temperature is a temperature 25° C. or less below the softening point or melting point of the aliphatic hydrocarbon lubricant, flowability of the aliphatic hydrocarbon lubricant is suppressed, and thereby a granulation operation tends to be facilitated, being preferable.

Granulation is usually performed, for example, using an instrument capable of mixing the phosphite (1), the aliphatic hydrocarbon lubricant and optionally an additive to produce a homogeneous mixture and adjusting the temperature of the mixture at a mixing process to 40 to 110° C., preferably a temperature about 3 to 25° C. below the softening point of the aliphatic hydrocarbon lubricant.

Examples of such an instrument include high speed rotation instruments such as a Henschel mixer, a super mixer, and a high speed mixer.

Specific examples of a granulation method include a method comprising placing the phosphite (1), the aliphatic hydrocarbon lubricant and, if necessary, an additive in a mixing machine such as a Henschel mixer, and then stirring and mixing the materials at a high speed; a method comprising spraying a heat-melted aliphatic hydrocarbon lubricant to the phosphite (1) and an additive optionally added while mixing, and then cooling the mixture while stirring; and the like.

Examples of a method of adjusting the granulation temperature to 40 to 110° C. include a method comprising heating a mixture to be granulated by using a heated water jacket attached to a Henschel mixer; a method comprising elevating the temperature by utilizing a shear heat which is generated due to high speed stirring; and the like.

Among the above described methods, a method comprising placing the phosphite (1), the aliphatic hydrocarbon lubricant and, if necessary, an additive in a mixing machine such as a Henschel mixer, and then stirring and mixing the materials at a high speed is simple from the standpoint of operation, and therefore is particularly preferable.

The granular composition thus obtained comprises fewer fine particles and therefore, the amount of dust raised from the granular composition is small and the granular composition has good flowability. The resulting granular composition may be subjected to a sieving step to remove fine particles. However, since the granular composition of the present invention comprises fewer particles, a sieving step may be omitted.

The composition of the present invention is suitable as an agent for preventing deterioration of a thermoplastic resin which is easily deteriorated by heat and light.

A thermoplastic resin used in the present invention is a mixture containing a high-molecular compound having a molecular weight of not less than 10,000 as a main component.

Examples of the thermoplastic resin include a polyolefin resin (polyethylene, polypropylene, ethylene-vinyl acetate copolymer etc.), a polystyrene resin (GP-PS, HI-PS, styrene-butadiene copolymer, acrylonitrile-styrene-butadiene terpolymer etc.), a polyamide resin (6 nylon, 12 nylon etc.), cyclic polyolefin, a chlorine-containing polymer (polyvinyl chloride, chlorinated rubber etc.), polyester (polyethylene terephthalate, polybutylene terephthalate etc.), polyurethane, an engineering plastic (polyphenylene ether, polycarbonate etc.) and the like.

The thermoplastic resin is preferably polyolefin such as polyethylene or polypropylene, and particularly preferred is polyethylene having a melt index (MI) of 0.01 to 100 as measured at 190° C. under a load of 2.16 kg or polypropylene having a melt index (MI) of 0.01 to 100 as measured at 230° C. under a load of 2.16 kg.

When the granular composition of the present invention is added to the thermoplastic resin, the resulting thermoplastic resin composition has improved processing stability and has improved coloring resistance.

The amount of the composition of the present invention to be added to the thermoplastic resin is usually in a range of 0.01 to 1 part by weight, preferably in a range of 0.02 to 0.5 part by weight, and more preferably in a range of 0.04 to 0.2 part by weight relative to 100 parts by weight of the thermoplastic resin. When the addition amount of the composition of the present invention is within the above described range, the processing stability of the resulting thermoplastic resin composition tends to be improved, being preferable.

The composition of the present invention is incorporated into the thermoplastic resin by, for example, a method comprising mixing the composition and the thermoplastic resin and then melt-kneading the mixture with a uniaxial or multi-axial extruder; a method comprising feeding a solution or suspension of the composition in a solvent to a solution of a polymerized thermoplastic resin, followed by evaporation, distillation or the like to remove the solvent, or the like.

The thermoplastic resin composition thus obtained can be processed into a product such as a film, a molded material or a pipe, and then used.

The composition of the present invention is useful as an agent for preventing deterioration of a thermoplastic resin such as polyolefin, and can reduce generation of dust caused when a phosphite is handled, for example, when a phosphite is added to a thermoplastic resin. In addition, when the composition of the present invention is added to a thermoplastic resin, a phosphite contained in the composition of the present invention is sufficiently dispersed in a thermoplastic resin, so that the resulting thermoplastic resin composition had improved coloring resistance.

Furthermore, according to the method of the present invention, it is possible to simply produce a granular composition which generates less dust.

EXAMPLES

Hereinafter, the present invention will be explained in more detail based on Examples, but it is needless to say the present invention is not limited to Examples.

In Examples, the following compounds were used: a phosphite (abbreviated as "1-1"): 6-[3-(3-t-butyl-4-hydroxy-5-methylphenyl)propoxy]-2,4,8,10-tetra-t-butyldibenz[d,f][1,3,2]dioxaphosphepine; an aliphatic hydrocarbon lubricant (abbreviated as "2-1"): polyethylene wax (manufactured by Sanyo Chemical Industries, Ltd.; Sanwax P-151, melting point 107° C.); glycerin monostearate (abbreviated as "2"); and a metal soap (abbreviated as "3"): calcium stearate.

Example 1

Production Example of Granular Composition

Into a mixing chamber of a Henschel mixer having a volume of 10 L which is equipped with a temperature sensor and a heated water jacket in the interior of the mixing chamber were placed 1 kg of the phosphite (1-1) and 50 g of the aliphatic hydrocarbon lubricant (2-1) as a binder. Subsequently, a liquid at 90° C. was passed through the heated water jacket, and high speed mixing was performed at a rotation number of 950 to conduct granulation. After 4 minutes and 20 seconds from the initiation of mixing, the temperature sensor in the interior of the mixing chamber indicated 84° C. (final temperature). Stirring was stopped, and 1 kg of a granular composition A was taken out from a discharge port.

Examples 2 to 4 and Comparative Examples 1 to 4

Granular compositions B to H were produced according to the same manner as that of Example 1 except that the compounds and amounts shown in Table 1 were used and granulation was performed under the jacket temperature and the final temperature of mixing shown in Table 1.

In Example 4 and Comparative Examples 2 and 3, 200 g of the metal soap (3) as an additive was placed into the mixing chamber, and granulation was performed.

Example 5

Production of Polypropylene Composition and Coloring Resistance of Resulting Polypropylene Composition One kilogram of polypropylene (MI: 3 g/10 min), 0.5 g of calcium stearate and 1 g of the granular composition A were dry-blended, and extruded at an extrusion temperature of 230° C. with a 30 mmΦ uniaxial extruder to obtain a pellet. The pellet was injection-molded at 230° C. to obtain a sheet of polypropylene (40×60×1 mm). The coloring resistance (ΔYI) before and after exposure of the polypropylene sheet to 650 ppm of an NOx gas was 1.07.

TABLE 1

| | Granular composition | Phosphite (Type) | Phosphite (Amount) | Binder (Type) | Binder (Amount) | Metal soap (Amount) | Jacket temperature | Final temperature |
|---|---|---|---|---|---|---|---|---|
| Example 1 | A | 1-1 | 1 kg | 2-1 | 50 g | Non-addition | 90° C. | 84° C. |
| Example 2 | B | 1-1 | 1 kg | 2-1 | 20 g | Non-addition | 95° C. | 84° C. |
| Example 3 | C | 1-1 | 1 kg | 2-1 | 10 g | Non-addition | 110° C. | 85° C. |
| Example 4 | D | 1-1 | 1 kg | 2-1 | 50 g | 3 (200 g) | 110° C. | 101° C. |
| Comparative Example 1 | E | 1-1 | 1 kg | 2-1 | 150 g | Non-addition | 90° C. | 81° C. |
| Comparative Example 2 | F | 1-1 | 1 kg | 2' | 150 g | 3 (200 g) | 70° C. | 68° C. |
| Comparative Example 3 | G | 1-1 | 1 kg | 2' | 50 g | 3 (200 g) | 70° C. | 69° C. |
| Comparative Example 4 | H | 1-1 | 1 kg | Non-addition | | Non-addition | 90° C. | 90° C. |

The Particle sizes of granular compositions obtained in Examples 1 to 4 and Comparative Examples 1 to 4 were measured. Results are shown in Table 2. About 5 g of a sample was subjected to measurement of particle size using a robot shifter (manufactured by Seishin Enterprise Co., Ltd) at a vibration level of 8, a shift time of 3 minutes and a pulse interval 1 second. A smaller amount of particles having a particle diameter of not more than 45 μm contained in a sample means that the sample contains fewer fine particles and the amount of dust raised when the sample is handled is smaller.

Assessment Method of Coloring Resistance (ΔYI):

The polypropylene sheet was exposed to 650 ppm of an NOx gas at about 25° C. for 7 days. Yellowness indexes (YI) of the sheet before and after exposure were measured. The coloring resistance of the polypropylene composition was assessed by a difference (ΔYI) between YI after exposure and YI before exposure.

Examples 6 to 8 and Comparative Examples 5 to 8

Polypropylene compositions were produced and their coloring resistance was assessed according to the same manner as that of Example 5 except that the granular compositions shown in Table 3 were used. Results together with a result of Example 5 are shown in Table 3. Smaller ΔYI means better coloring resistance.

TABLE 2

| Example No. | Granular composition | % by weight of particles having a particle diameter of not more than 45 μm | Average particle diameter (DP50) |
|---|---|---|---|
| Example 1 | A | 8 | 96 |
| Example 2 | B | 7 | 110 |
| Example 3 | C | 8 | 99 |
| Example 4 | D | <1 | 218 |
| Comparative Example 1 | E | 6 | 116 |
| Comparative Example 2 | F | <1 | 161 |
| Comparative Example 3 | G | 14 | 73 |
| Comparative Example 4 | H | >20 | <62 |

TABLE 3

| Example No. | Weight of polypropylene | Granular composition Type | Granular composition Weight | Coloring resistance (ΔYI) |
|---|---|---|---|---|
| Example 5 | 1 kg | A | 1 g | 1.07 |
| Example 6 | 1 kg | B | 1 g | 1.05 |
| Example 7 | 1 kg | C | 1 g | 0.92 |
| Example 8 | 1 kg | D | 1 g | 1.00 |
| Comparative Example 5 | 1 kg | E | 1 g | 1.10 |
| Comparative Example 6 | 1 kg | F | 1 g | 1.67 |
| Comparative Example 7 | 1 kg | G | 1 g | 1.23 |
| Comparative Example 8 | 1 kg | H | 1 g | 1.15 |

Example 9

Production of Polyethylene Composition and Processing Stability of Resulting Polyethylene Composition One kilogram of linear low density polyethylene (MI: 1 g/10 min), 3 g of the granular composition A were dry-blended, and extruded at an extrusion temperature of 210° C. with a 30 mmΦ uniaxial extruder to obtain a pellet. The melt-mass flow rate (MFR) of the pellet was measured at 190° C. and under a load of 5 kg, and adopted as an initial MFR. The pellet was extruded repetitively three times at 250° C. Then, the MFR (190° C., 5 kg) of the pellet was measured to assess the processing stability of the polyethylene composition.

Assessment Method of Processing Stability (MFR (g/10 min)):

JIS K 7210 (1976) (method A) was used at 190° C. and under a load of 5 kg.

Examples 10 to 12 and Comparative Examples 9 to 10

Polyethylene compositions were produced and their processing stability was assessed according to the same manner as that of Example 9 except that the granular compositions shown in Table 4 were used. Results together with a result of Example 9 are shown in Table 4. An MFR value after repeated extrusion nearer an initial MFR value means better processing stability.

TABLE 4

|  | Weight of polyethylene | Granular composition Type | Granular composition Weight | Initial MFR | MFR after three times extrusion |
|---|---|---|---|---|---|
| Example 9 | 1 kg | A | 3.0 g | 3.5 | 3.6 |
| Example 10 | 1 kg | A | 1.5 g | 3.5 | 3.5 |
| Example 11 | 1 kg | A | 1.0 g | 3.5 | 3.4 |
| Example 12 | 1 kg | A | 0.3 g | 3.5 | 2.4 |
| Comparative Example 9 | 1 kg | Non-addition | — | 3.2 | 2.1 |
| Comparative Example 10 | 1 kg | A | 15 g | 3.7 | 3.8 |

Example 13

Production of Polystyrene Composition

One kilogram of polystyrene and 1 g of the granular composition A are dry-blended, and extruded with a 30 mmΦ uniaxial extruder to obtain a pellet. Then, the resulting pellet is injection-molded to obtain a sheet of polystyrene which has excellent coloring resistance.

What is claimed is:

1. A phosphite composition comprising 100 parts by weight of a phosphite represented by the formula (1):

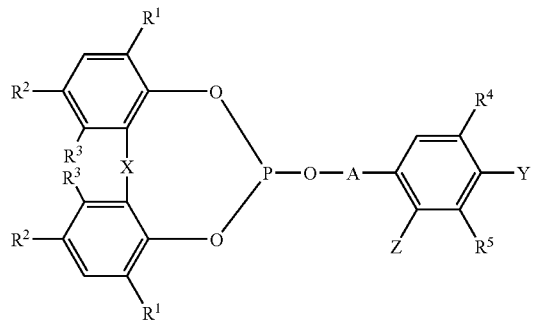

(1)

wherein $R^1$, $R^2$, $R^4$ and $R^5$ independently represent a hydrogen atom, an alkyl group of 1 to 8 carbon atoms, a cycloalkyl group of 5 to 8 carbon atoms, an alkylcycloalkyl group of 6 to 12 carbon atoms, an aralkyl group of 7 to 12 carbon atoms or a phenyl group, $R^3$ represents a hydrogen atom or an alkyl group of 1 to 8 carbon atoms, X represents a single bond, a sulfur atom or a —$CHR^6$— group, in which $R^6$ represents a hydrogen atom, an alkyl group of 1 to 8 carbon atoms or a cycloalkyl group of 5 to 8 carbon atoms, A represents an alkylene group of 2 to 8 carbon atoms or a *—$COR^7$— group, in which $R^7$ represents a single bond or an alkylene group of 1 to 8 carbon atoms, and the symbol * represents a point being linked with the oxygen atom of the >P—O— group in the formula (1), one of Y and Z represents a hydroxyl group, an alkoxy group of 1 to 8 carbon atoms or an aralkyloxy group of 7 to 12 carbon atoms, and the other represents a hydrogen atom or an alkyl group of 1 to 8 carbon atoms, when Y is a hydroxyl group, one of $R^4$ and $R^5$ represents an alkyl group of 3 to 8 carbon atoms, a cycloalkyl group of 5 to 8 carbon atoms, an alkylcycloalkyl group of 6 to 12 carbon atoms, an aralkyl group of 7 to 12 carbon atoms or a phenyl group, and $R^1$, $R^2$ and $R^3$ may be the same or different;

and 0.5 to 8 parts by weight of an aliphatic hydrocarbon lubricant having a softening point or a melting point of not higher than 115° C., wherein the content of the phosphite represented by the formula (1) in said composition is 30 to 99.5% by weight, wherein the composition is a granular composition, and wherein the composition comprises not more than 10% by weight of components having a particle diameter of not more than 45 μm.

2. A method for producing a phosphite composition, which comprises mixing 100 parts by weight of a phosphite and 0.5 to 8 pails by weight of an aliphatic hydrocarbon lubricant having a softening point or a melting point of not higher than 115° C. and granulating the mixture at a temperature range of 40 to 110° C.,
wherein the phosphite is represented by formula (1):

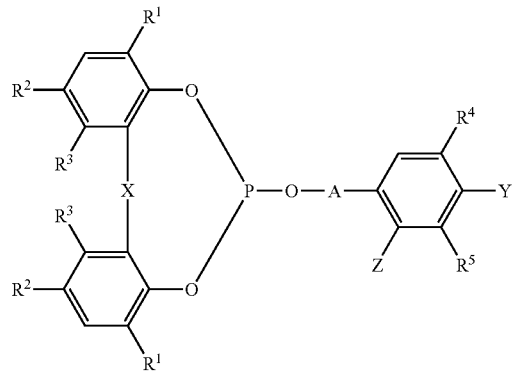

wherein $R^1$, $R^2$, $R^4$ and $R^5$ independently represent a hydrogen atom, an alkyl group of 1 to 8 carbon atoms, a cycloalkyl group of 5 to 8 carbon atoms, an alkylcycloalkyl group of 6 to 12 carbon atoms, an aralkyl group of 7 to 12 carbon atoms or a phenyl group, $R^3$ represents a hydrogen atom or an alkyl group of 1 to 8 carbon atoms, X represents a single bond, a sulfur atom or a —$CHR^6$— group, in which $R^6$ represents a hydrogen atom, an alkyl group of 1 to 8 carbon atoms or a cycloalkyl group of 5 to 8 carbon atoms, A represents an alkylene group of 2 to 8 carbon atoms or a *—$COR^7$— group, in which $R^7$ represents a single bond or an alkylene group of 1 to 8 carbon atoms, and the symbol * represents a point being linked with the oxygen atom of the >P—O— group in the formula (1), one of Y and Z represents a hydroxyl group, an alkoxy group of 1 to 8 carbon atoms or an aralkyloxy group of 7 to 12 carbon atoms, and the other represents a hydrogen atom or an alkyl group of 1 to 8 carbon atoms, when Y is a hydroxyl group, one of $R^4$ and $R^5$ represents an alkyl group of 3 to 8 carbon atoms, a cycloalkyl group of 5 to 8 carbon atoms, an alkylcycloalkyl group of 6 to 12 carbon atoms, an aralkyl group of 7 to 12 carbon atoms or a phenyl group, and $R^1$, $R^2$ and $R^3$ may be the same or different.

3. The method according to claim 2, wherein granulation is carried out at a temperature 3 to 25° C. below the softening point or melting point of the aliphatic hydrocarbon lubricant.

4. A method of stabilizing a thermoplastic resin, which comprises incorporating 0.01 to 1 part by weight of a phosphite composition into 100 parts by weight of a thermoplastic resin, wherein the composition comprises 100 parts by weight of a phosphite represented by the formula (1):

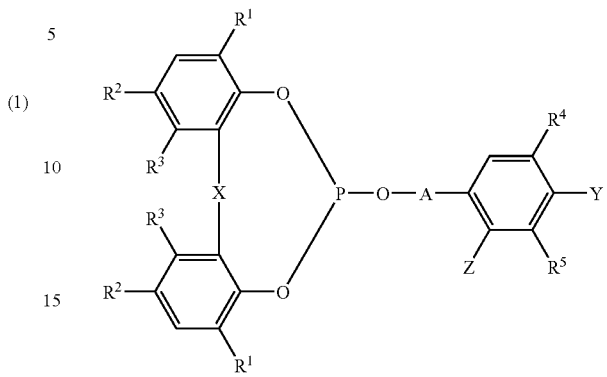

wherein $R^1$, $R^2$, $R^4$ and $R^5$ independently represent a hydrogen atom, an alkyl group of 1 to 8 carbon atoms, a cycloalkyl group of 5 to 8 carbon atoms, an alkylcycloalkyl group of 6 to 12 carbon atoms, an aralkyl group of 7 to 12 carbon atoms or a phenyl group, $R^3$ represents a hydrogen atom or an alkyl group of 1 to 8 carbon atoms, X represents a single bond, a sulfur atom or a —$CHR^6$— group, in which $R^6$ represents a hydrogen atom, an alkyl group of 1 to 8 carbon atoms or a cycloalkyl group of 5 to 8 carbon atoms, A represents an alkylene group of 2 to 8 carbon atoms or a *—$COR^7$— group, in which $R^7$ represents a single bond or an alkylene group of 1 to 8 carbon atoms, and the symbol * represents a point being linked with the oxygen atom of the >P—O— group in the formula (1), one of Y and Z represents a hydroxyl group, an alkoxy group of 1 to 8 carbon atoms or an aralkyloxy group of 7 to 12 carbon atoms, and the other represents a hydrogen atom or an alkyl group of 1 to 8 carbon atoms, when Y is a hydroxyl group, one of $R^4$ and $R^5$ represents an alkyl group of 3 to 8 carbon atoms, a cycloalkyl group of 5 to 8 carbon atoms, an alkylcycloalkyl group of 6 to 12 carbon atoms, an aralkyl group of 7 to 12 carbon atoms or a phenyl group, and $R^1$, $R^2$ and $R^3$ may be the same or different;

and 0.5 to 8 parts by weight of an aliphatic hydrocarbon lubricant having a softening point or a melting point of not higher than 115° C., wherein the content of a phosphite represented by the formula (1) in said composition is 30 to 99.5% by weight, and wherein the thermoplastic resin is polyolefin.

5. The composition according to claim 1, wherein the aliphatic hydrocarbon lubricant is at least one kind of aliphatic hydrocarbon lubricant selected from the group consisting of liquid paraffin, paraffin having a melting point of 40 to 70° C., and polyethylene wax having a softening point of not higher than 115° C.

6. A method of stabilizing a thermoplastic resin, which comprises incorporating 0.01 to 1 part by weight of the composition according to claim 1 into 100 parts by weight of a thermoplastic resin.

7. The method according to claim 6, wherein the aliphatic hydrocarbon lubricant is at least one kind of aliphatic hydrocarbon lubricant selected from the group consisting of liquid paraffin, paraffin having a melting point of 40 to 70° C., and polyethylene wax having a softening point of not higher than 115° C.

8. The method according to claim 4, wherein the aliphatic hydrocarbon lubricant is at least one kind of aliphatic hydrocarbon lubricant selected from the group consisting of liquid paraffin, paraffin having a melting point of 40 to 70° C., and polyethylene wax having a softening point of not higher than 115° C.

9. The method according to claim 4, wherein the composition is a granular composition.

10. The method according to claim 9, wherein the composition comprises not more than 10% by weight of components having a particle diameter of not more than 45 μm.

11. The method according to claim 9, wherein the aliphatic hydrocarbon lubricant is at least one kind of aliphatic hydrocarbon lubricant selected from the group consisting of liquid paraffin, paraffin having a melting point of 40 to 70° C., and polyethylene wax having a softening point of not higher than 115° C.

12. The method according to claim 11, wherein the composition comprises not more than 10% by weight of components having a particle diameter of not more than 45 μm.

* * * * *